United States Patent [19]

Battaglia

[11] Patent Number: 5,088,037
[45] Date of Patent: Feb. 11, 1992

[54] PORTABLE RESCUE ADMINISTRATION AID DEVICE

[76] Inventor: Anthony Battaglia, 363 Pharmacy Avenue, Scarborough, Ontario, Canada, M1L 3G4

[21] Appl. No.: 497,264

[22] Filed: Mar. 22, 1990

[51] Int. Cl.⁵ .................. G06F 15/42; G09B 23/28
[52] U.S. Cl. ..................... 364/413.01; 434/265
[58] Field of Search ............ 364/413.01, 413.02, 364/413.03; 434/226, 265, 262

[56] References Cited

U.S. PATENT DOCUMENTS

| D. 243,250 | 2/1977 | Hazama | 364/708 X |
|---|---|---|---|
| 4,290,114 | 9/1981 | Sinay | 364/900 |
| 4,360,345 | 11/1982 | Hon | 434/262 |
| 4,465,077 | 8/1984 | Schneider | 128/738 |
| 4,489,387 | 12/1984 | Lamb et al. | 364/514 |
| 4,583,524 | 4/1986 | Hutchins | 434/265 X |
| 4,588,383 | 5/1986 | Parker et al. | 434/265 |
| 4,797,104 | 1/1989 | Laerdal et al. | 434/265 |
| 4,828,501 | 5/1989 | Ingenito et al. | 434/265 |
| 4,839,822 | 6/1989 | Dormond et al. | 364/513 |
| 4,842,531 | 6/1989 | Takemura | 439/165 |
| 4,863,385 | 9/1989 | Pierce | 434/265 |

*Primary Examiner*—Dale M. Shaw
*Assistant Examiner*—David Huntley
*Attorney, Agent, or Firm*—David W. Wong

[57] ABSTRACT

This rescue administration aid device is a portable unit which may be worn on a rescuer's wrist. It is operative in response to parameter entries by the rescuer according to the victim's condition to provide sequential procedural displays of medical standard rescue steps for assisting the rescuer in carrying out the correct rescue operation. The standard rescue procedure is stored in a microprocessor which, if necessary, can be re-programmed to update to a new rescue standard procedure. It includes a recall feature operative for reverse searching of any desired step in the display if the condition of the victim changes during the rescue operation. Additionally, distinct tone signals are emitted at selected steps of the rescue operation procedure to assist the rescuer in memorizing and conducting such steps in the rescue.

14 Claims, 4 Drawing Sheets

PORTABLE RESCUE ADMINISTRATION AID DEVICE

BACKGROUND OF THE INVENTION

This invention relates to rescue administration aid device and particularly relates to such a device having a display operative to provide sequential displays of rescue steps for carrying out the rescue operation on an unconscious victim.

In any rescue operation, particularly, in the rescue of an unconscious victim, it is of paramount importance for the rescuer to administer aid on the victim as soon as possible. Normally, if proper rescue operations are applied to a victim, the chances of survival or recovery of the victim would be much improved. In order to carry out the rescue operation effectively the rescuer must follow the steps set out in medical standard rescue procedure in response to the condition of the victim. Standard rescue procedures are well developed in the medical field and are beyond the scope of this disclosure, except so far as may be necessary to explain the nature and application of the present invention. Studies have shown that even amongst professional rescue operators such as paramedics, firemen, and nurses, very few people, by percentage. Can remember the proper rescue sequence or procedure precisely. This is further complicated by the changing procedure due to improved standards such that new procedures are established. As the procedure becomes more and more complex, it, in turn, becomes harder and harder to be memorized by the rescue operator. Moreover, the memory retention of the rescue procedure by the rescuer is further hampered by the chaotic circumstances in an emergency situation normally encountered by the rescuer. Nowadays, as more and more laypersons are receiving training in the cardiopulmonary rescue operation, the need for an effective aid has become more and more demanding.

Attempts have been made to provide devices to assist the cardiopulmonary rescuer to perform the rescue operation properly One of such devices as shown in U.S. Pat. No. 4,451,158 to Selwyn et al, is in the form of a timer with various coded pattern displays at predetermined time intervals to indicate various stages in the rescue operation. The main drawback of such device is that confusion may still arise for the rescuer to memorize which procedural step is related to which code. Furthermore, such device could only provide preset procedure without taking in account the necessity of procedural change when the victim's condition changes during the rescue operation.

Another device such as that shown in U.S. Pat. No. 4,588,383 to Parker et al, provides voice instructions solely for the rescuer to carry out the rescue operation. Such device is highly impractical due to the inability of the rescuer to listen to the instructions in a normally noisy environment in an emergency rescue such as in outdoors or in a factory environment.

Furthermore, most of the known devices are bulky in size, not portable to be located conveniently beside the victim at the rescue cite, and are complex to operate.

SUMMARY OF THE INVENTION

The principal object of the present invention is to provide a portable device which can be conveniently located beside the victim or directly worn on the wrist of the rescuer to assist the rescuer to carry out the rescue operation.

It is another object of the present invention to provide a rescue administration aid device which displays step by step instructions sequentially in response to the condition of the victim.

It is another object of the present invention to provide a rescue administration aid device operative to assist one or two rescuers to perform the required rescue operation on a victim of a selected age group.

It is yet another object of the present invention to provide a rescue administration aid device which is operative to recall any selected step in the rescue operation by the rescuer.

it is a further object of the present invention to provide a rescue administration aid device which includes distinctive audible tone signals in addition to the visual procedural displays to enhance the rescuer's retention span of the required operation.

It is still a further object of the present invention to provide a rescue administration aid device in which the rescue instructions can be easily modified, if necessary, to update to a new rescue operation standard.

it is still yet another object of the present invention to provide a rescue administration aid device which can be used for training of rescuers and which can be coupled to other electronic medical storage means for retrieving medical datas.

in general these and other objects of the invention that will appear as the description proceeds are achieved by a rescue administration aid device comprising a screen display means operative to provide lighted display of sequential instructions of a predetermined rescue procedure according to condition of a victim observed by at least one rescue operator, an electronic microprocessor means programmable to store said instructions and operative to actuate said display means for displaying said instructions, first parameter means coupled to said microprocessor means and being operative to prompt said microprocessor means for actuating said display means to display. Instructions for a selected number of rescue operators in the rescue operation, second parameter means coupled to said microprocessor means and being operative to prompt said microprocessor means for actuating said display means to display instructions suitable for a selected age group of victim, a plurality of selection means coupled to said microprocessor means and being selectively operative in association with said first parameter means and second parameter means, by said rescuer whereby said display means displays said sequential instructions.

DESCRIPTION OF THE DRAWINGS

Other objects of this invention will appear in the following description and appended claims, reference being made to the accompanying drawings forming a part of the specification.

DETAILED DESCRIPTION OF THE PREFERRED EMBODIMENTS

Figure 1:
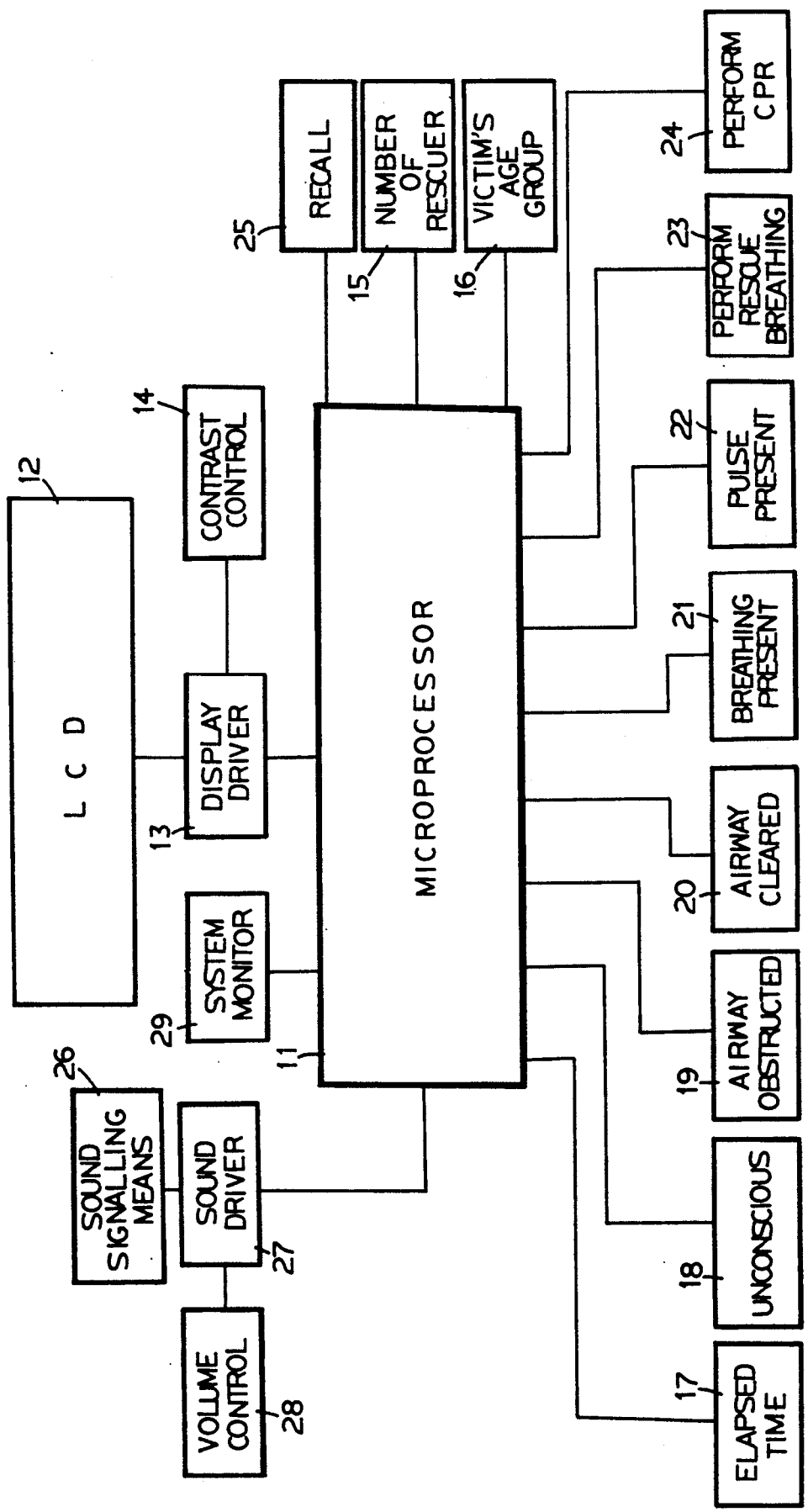
FIG. 1 is a schematic diagram of the physical components of a preferred embodiment of the present invention.

The rescue administration aid device of the present invention is generally shown in the schematic diagram in FIG. 1. The device 10 has a single main microprocessor 11 which can be preprogrammed to store a series of rescue operation instructions according to the medical standard. Since all the instructions are stored in a single microprocessor 11, it can be easily and simply reprogrammed or replaced with another microprocessor when and if the rescue operation standard has been modified. The instructions in the microprocessor 11 may be displayed in an electronic display means 12 through display driver 13. The display means 12 preferably is a liquid crystal display, commonly referred to as LCD display which can provide clear graphic and alphanumerical display for showing an easy to follow and relatively detail instructions for the rescuer in carrying out the proper rescue operation. With the provision of such displayed instructions, the device may also be used by a deaf person. The LCD display provides a wide viewing angle without distortion and it has a low power requirement and yet offers a very fast response time from milliseconds to two seconds maximum. The contrast and brightness of the display may be adjusted by the contrast control 14.

The parameters of the display instructions are set by parameter selectors 15 and 16. The parameter selector 15 is for inputting to the microprocessor 11 the command whether or not the rescue instruction to be display is for one or two rescuers. Such information is important since the instructions for one rescuer and two rescuers are different in some of the steps in the rescue procedure such as in performing the cardiopulmonary resuscitation, commonly referred to as CPR. The parameter selector 16 is for selecting the instruction suitable for the particular age group of the victim. The instructions can be separated generally into three groupings: the first group is for an infant victim up to 1 year old; the second group is for a victim between the age of 1 to 8 years old; and the third group is for a victim 8 years old and over. Such groupings are set by the rescue standard which provides a different procedure for each of the group.

The microprocessor 11 has an internal timer means which will be actuated as soon as the device 10 is turned on. Once actuated, the timer will continue to keep the time during the entire rescue operation. The time elapsed at any instance after the device 10 is energized, may be displayed by actuating a time retrieving means 17. Such elapsed time information is very important particularly when the victim may finally be transferred to an emergency medical facility through the Emergency Medical System. The elapsed time will promptly provide the indication to the attending physician the amount of time in which basic rescue operation has been applied to the victim so that suitable medical procedure may be undertaken. The microprocessor 11 is commanded through a plurality of condition selectors for entering therein the condition of the victim in order for the LCD display 12 to display the suitable instruction in response to the selected condition of the victim. The first condition selector 18 is to input to the microprocessor 11 if the victim is actually unconscious. The second and third selector 19 and 20 may then be operated to select the instruction for whether the victim's airway is obstructed or clear. The fourth selector 21 is to enter into the microprocessor 11 if breathing is present, while the fifth selector 22 is to inform the microprocessor 11 the pulse integrity of the victim. After the victim's condition has been entered by selectors 18 through 22, the rescuer will be instructed to actuate the actuating operation means 23 and/or 24 selectively to commence the necessary rescue operation. The microprocessor 11 in response to the actuation of the actuating operation means 23 and/or 24 will send the required instructions through the display driver 13 to display the rescue procedure sequentially in the LCD display 12 for prompting the rescuer to carry out the necessary rescue operation. Alternatively, in view of the deteriorating condition of the victim, the rescuer may actuate the actuating operation means 23 and/or 24 immediately to commence the performance of rescue breathing operation and/or the CPR.

In the basic embodiment, the rescue instruction consists of 20 messages displayed sequentially. Any particular message in the displayed instruction may be recalled by the rescuer by actuating the recall means 25 which will reverse the sequential display until the required message is reached. Such function enables the rescuer to selectively repeat a message if accidentally the message is missed by the rescuer. Also, it serves the important function for the rescuer to re-check the suitable step in the rescue procedure, if and when the victim's condition changes during the rescue operation.

The messages in the rescue instruction are additionally highlighted with four distinct tone signals emitted by a sound signal means 26 actuated by the microprocessor 11 through a sound driver 27. It can be appreciated that such sound signals are not essential to the rescue operation, since the rescue instructions are fully displayed; however, they may assist the rescuer to familiarize himself with the various steps in the rescue operation particularly during the training of such rescuer in carrying out the necessary steps at the proper time. Furthermore, it may facilitate the use of the device by a blind rescuer. Four distinct tones are provided in the present invention, namely, a 400 hertz tone an 800 hertz tone, a 1200 hertz tone, and a 3300 hertz tone to highlight the steps such as "compression", "get ready", "ventilation", and "new message". The volume of the sound signal is controlled by adjusting the volume control means 28.

The device 10 is provided with a system monitor means 29 coupled to the microprocessor 11 which is automatically actuated when the device 10 is turned on for providing the self-diagnostic function of the system, and any malfunction and/or low battery condition will be displayed on the screen of the LCD 12.

Figure 2:
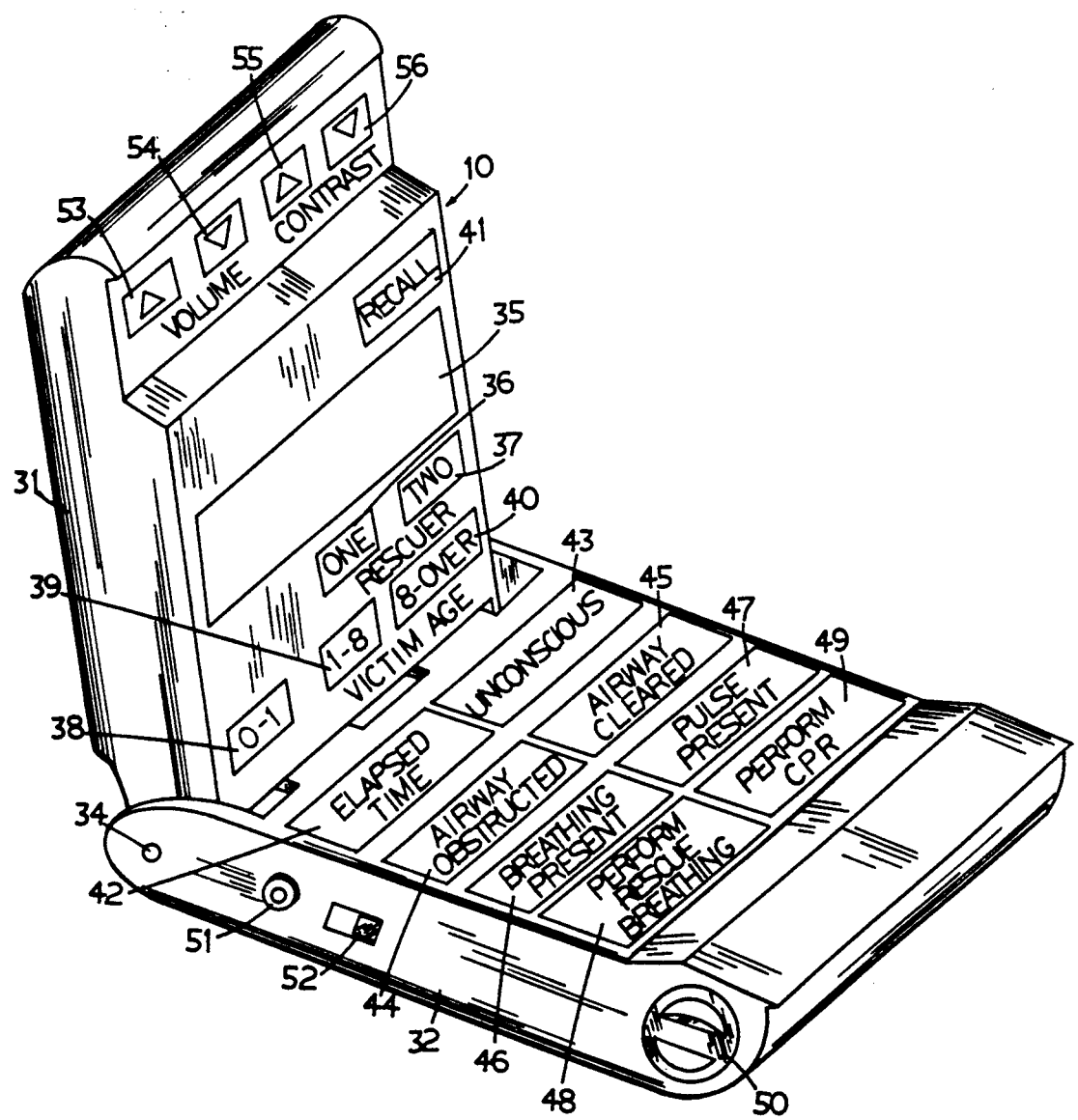
FIG. 2 is a perspective front elevation view of the portable rescue administration aid device according to the present invention.

The administration aid device 10 is housed in a casing 30 consisting of an upper casing 31 and a lower casing 32 hingedly coupled together with a hinge arrangement 34, so that, normally when not in use, the upper casing 31 can be folded downwardly over the lower casing 32 to form a closed box. The hinge arrangement 34 may be provided with several click stops to maintain the upper casing 31 in several selected opened positions. The display screen 35 of the LCD display is provided in the upper casing 31 so that at the various opened positions the messages on the screen are clearly legible to the rescuer. Non-slip rubber pads may be provided at the bottom of the lower casing 32 to prevent the device from sliding over a surface on which it is resting. Also a removable band arrangement may be provided such that the device 10 may be worn on the rescuer's wrist. Such provision allows the rescuer to view the display messages conveniently while performing the rescue operation. The actuation switches 36 and 37 for entering the number of rescuer in the rescue operation are located directly below the display screen 35. The age group actuation switches 38, 39 and 40 are preferably located below the rescuer selection switches 36 and 37 as best shown in FIG. 2. A recall function switch 41 is conveniently located above the display screen 35. When the recall function switch 41 is operated, it actuates the recall means to command the microprocessor 11 to operate the LCD display in a reverse sequence such that the rescuer can recall any desired message in the instruction sequence if so desired. The display will commence again from the selected desired message when the recall function switch 41 is released thereat.

The condition selector means are operative by selection switches 42 through 47 located in the lower casing 32. The first selector switch 42 is for displaying the elapsed time when the device is first turned on until the time the selector switch 42 is pressed. This function provides a record and indication of the time spent by the rescuer in and procedure during the rescue operation. Such information is very important if the victim subsequently may be transfer red to an emergency medical facility through the Emergency Medical System. The second selector switch 43 is for actuating the condition selector 18 to inform the microprocessor 11 of whether or not the victim is actually in an unconscious state or is merely in a temporary painted state. The third and fourth selector switches 44 and 45 can be selectively actuated to operate the condition selectors 19 and 20 to set the condition of whether or not the victim's airway is clear of obstruction. The fifth selector switch 46 Is for operating the condition selector 21 to set the breathing condition of the victim observed by the rescuer. The sixth selector switch 47 is for actuating the condition selector 22 to select the condition if the victim's pulse can be detected by the rescuer. The generation switches 48 and 49 located at the bottom row of the lower casing 32 may be actuated to turn on the operation means 23 and 24 to prompt the microprocessor 11 to send the appropriate rescue instructions of performing breathing rescue operation and CPR operation to the LCD display 12.

A compartment with a removable cover 50 may be located at the side of the front end of the lower casing 32 to house a battery, or alternatively the compartment may be provided at the hinge portion therein. Also, a second similar compartment may additionally be provided at the opposite side of the lower casing 32 to house a spare battery. It can be appreciated by those skilled in the art that due to the low energy consumption of the LCD display and the electronic components used in the present device, a small size long life lithium battery can be used for operating the device. Such battery, despite of its small size, has an operating life under normal use of about 10 years. An AC adaptor socket 51 is provided at the side of the lower casing 32 such that the device may alternatively be operated with an external AC adaptor. The main ON/OFF switch 52 for the device may also be located at the side of the lower casing 32.

The volume of the audio tone signal generated by the sound signalling means 26 can be adjusted by operating the volume increase button 53 or the volume decrease button 54 respectively located at the upper portion of the upper casing 31. The contrast and legibility of the display in the LCD display 12 may be also adjusted by operating the contrast increase button 55 and contrast decrease button 56 respectively, which are also located at the upper portion of the upper casing 31.

Figure 3:
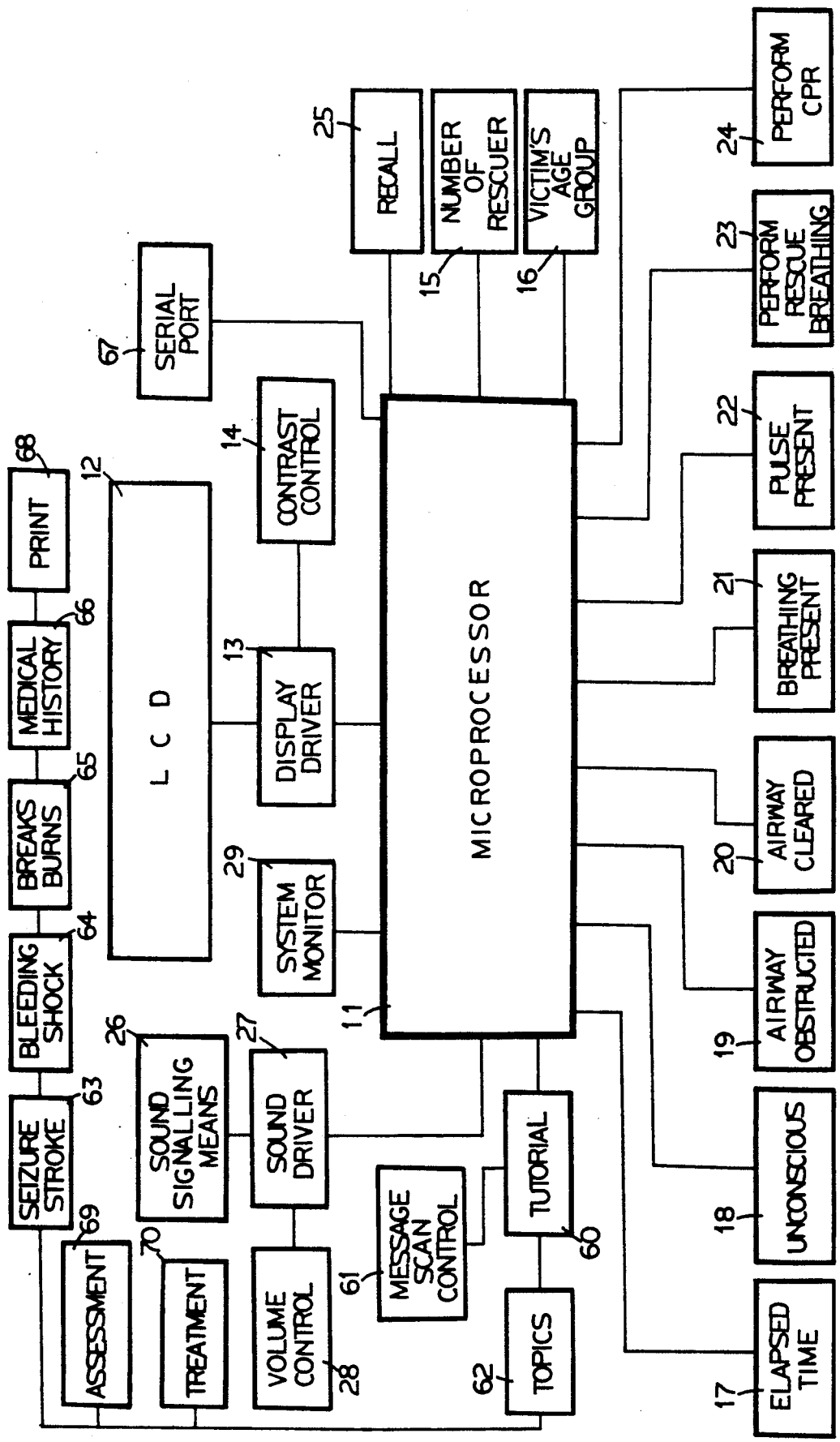
FIG. 3 is a schematic diagram of another embodiment of the present invention including data storage and retrieving means suitable also for training and reference purposes.

The basic embodiment of the device of the present invention as described above is primarily intended for use as a rescue administration aid for a rescuer in performing the rescue operation in the field; in practical application, it may also serve as an extremely helpful tool for training new rescuers of the proper rescue operation. The training capability of the device is further enhanced by the embodiment shown in FIGS. 3 through 5, in which a tutorial selector 60 is incorporated in the system. The tutorial selector 60 is coupled to the microprocessor 11 such that at any stage of the display of the victim's condition or at any step in the sequential instructions the tutorial selector 60 may be actuated to display an explanation message of that particular condition or step. The message may then be scanned by activating the message scan control 61. A number of typical topics of particular interest to rescue operations may also be selected in the tutorial mode of the device by the functioning of the topics selection means 62. The topics may include, for example, "SEIZURE STROKE", "BLEEDING SHOCK", "BREAKS BURNS", "MEDICAL HISTORY" conditions stored in auxiliary storage means 63, 64, 65 and 66 respectively. The message displayed in any of the above topics may be sent to an external printer connected to the device 10 through an external serial port 67 coupled to the microprocessor 11, by operating the print command selector 68. Moreover, assessment means 69 and treatment means 70 coupled to the topics selection means 62 and may be operated in each display to provide further assessment and treatment procedures for each selected condition.

Figure 4:
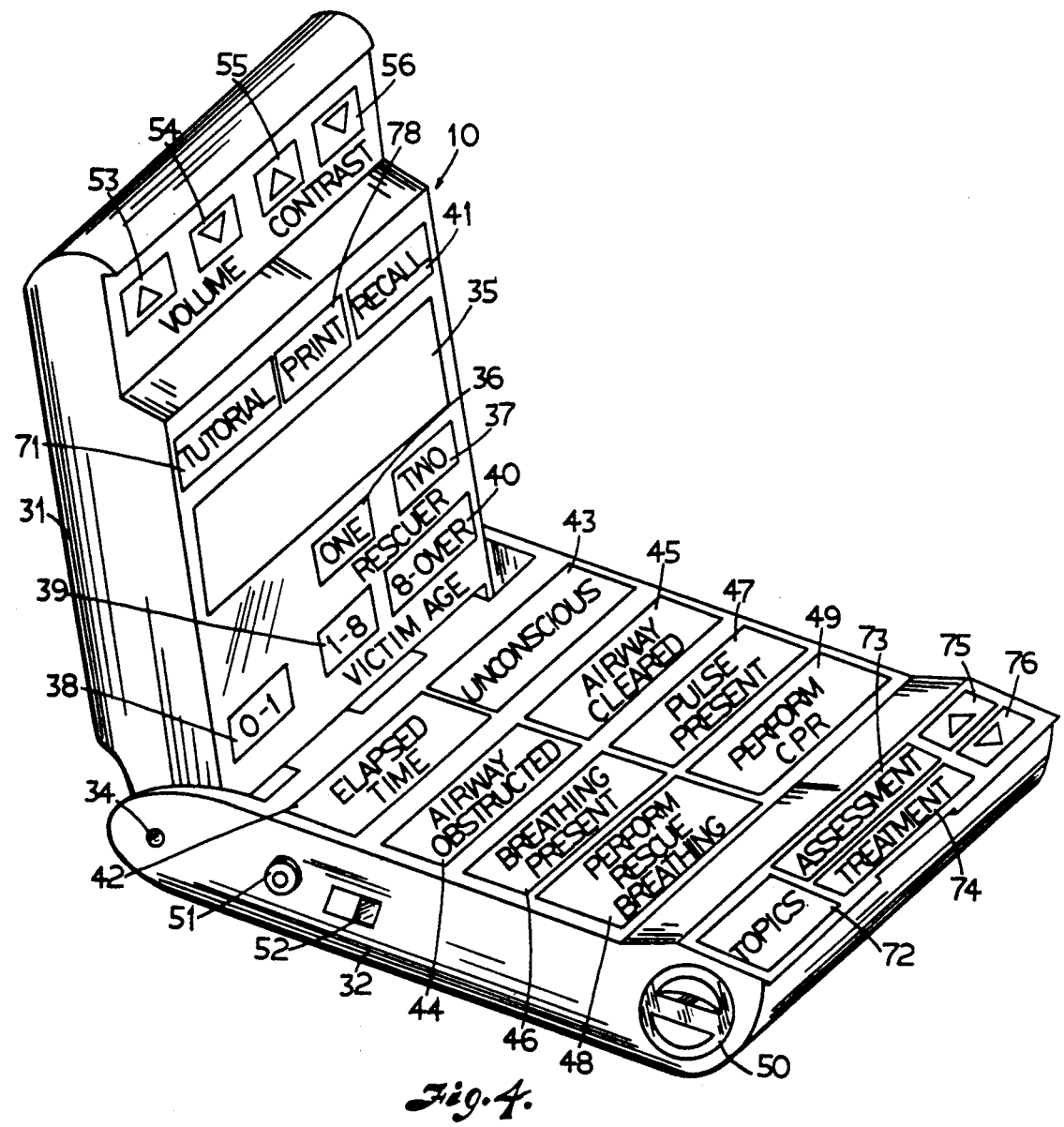
FIG. 4 is a perspective front elevation view of the device according to the present invention including the training and reference features

As shown in FIG. 4 the tutorial mode of the device 10 may be obtained by the actuation of the tutorial selector switch 71 provided at the upper casing 31. The topics selection switch 72 can be provided at the front end portion of the lower casing 32 together with the assessment and treatment selector switches 73 and 74 respectively. Also, the message scan selector switches 75 and 76 can be incorporated at the same front end portion of the lower casing 32.

Figure 5:
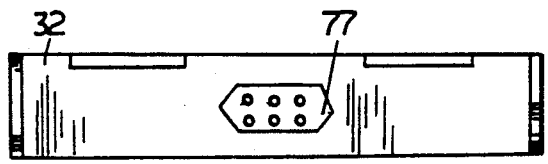
FIG. 5 is an isolated rear elevation view of the lower casing of the device showing the provision of a connection port for connecting the device to external peripheral devices.

The external serial port 77 can be conveniently located at the rear end of the lower casing 32 as best shown in FIG. 5 for connecting the device 10 to external peripheral devices for transfer of datas or data print out by a printer. The printing function can be activated by the actuation of the print selector switch 78 located at the upper casing 31.

While the principles of the invention have been made clear in illustrative embodiments, there will be immediately obvious to those skilled in the art that many modifications of structure, arrangement, proportions, the elements, materials, and components used in the practice of the invention, and otherwise, which are particularly adopted for specific environments and operative requirements without departing from those principles. The appended claims are intended to cover and embrace any and all such modifications, within the limits only of the true spirit and scope of the invention.

What is claimed is:

1. A compact portable rescue operation administration aid device, comprising:
   a foldable casing including an upper casing member and a lower casing member hingedly connected to one another at a hinge arrangement means,
   a microprocessor means disposed in said lower casing member, said microprocessor means being programmable to store a series of rescue administration instructions according to physical conditions of a victim observed by the rescuer,
   a display means disposed in said upper casing member, said display means being coupled to said microprocessor means and having a display screen, and being operative by said microprocessor means to display sequentially a selective series of readable messages of said rescue instructions,
   a plurality of parameter input means disposed in said upper casing member, and operative to set said microprocessor means for actuating said display means to display sequentially said selective readable messages for prompting selectively one and two rescuers to perform said rescue operation on a victim of a selected age group,
   a plurality of condition selection means disposed in said lower casing member, and operative in association with said parameter input means to set said microprocessor means for actuating said display means to display sequentially said selected readable messages in response to said victim's physical conditions.

2. A rescue operation administration aid device according to claim 1 wherein said display means is a liquid crystal display device.

3. A rescue operation administration aid device according to claim 2 wherein said selection means includes a time retrieving means operative to actuate said display means via said microprocessor means to display the elapsed time since the device was first actuated in a rescue operation.

4. A rescue operation administration aid device according to claim 3 wherein said selection means include a first input means coupled to said microprocessor means and operative to notify said microprocessor means of the conscious state of said victim, a second input means and a third input means coupled to said microprocessor means and operative to notify said microprocessor means of whether said victim has an obstructed airway, a fourth input means and a fifth input means coupled to said microprocessor means and operative to send signals to said microprocessor means to indicate the presence of breathing and pulse in said victim.

5. A rescue operation administration aid device according to claim 4 including a plurality of auxiliary data storage means operative for storing training and reference information of selected standard rescue operation, tutorial means coupled to said microprocessor means and said data storage means and being operative to activate said display means for displaying said information.

6. A rescue operation administration aid device according to claim 5 including a topics means coupled to said tutorial means and being operative to retrieve a selected information from said storage means for display by said display means.

7. A rescue operation administration aid device according to claim 6 including an assessement selector means and a treatment selector means coupled to said topics means and being operative selectively to activate said display means for displaying assessment and treatment for a selected victim condition.

8. A rescue operation administration aid device according to claim 7 including a system monitor means coupled to said microprocessor means and being operative when said device is activated to provide a self diagnostic procedure and to activate said display means to display and malfunction condition and battery condition.

9. A rescue operation administration aid deice according to claim 8 including a sound signalling means disposed in said upper casing member and coupled to said microprocessor means, said sound signalling means being operative to emit predetermined tone signals in association with selected messages when said rescue instructions are being sequentially displayed by said display means.

10. A rescue operation administration aid device according to claim 9 including a recall means provided at said upper casing member and connected to said microprocessor means, said recall means being operative by said rescuer to reverse the sequence of said sequentially displayed instructions to recapture a selected message in said instructions.

11. A rescue operation administration aid device according to claim 10 including a constrast adjusting means located in said upper casing member and operative to adjust the visibility of said display.

12. A rescue operation administration aid device according to claim 11 including a securing means removably mounted at a bottom surface of said lower casing member and operative for wearing said device on the wrist of said rescuer.

13. A rescue operation administration aid device according to claim 12 including a connecting port means located in said lower casing member and being operative for connecting said device to a selected peripheral device.

14. A rescue operation administration aid device according to claim 13 wherein said peripheral device is a printer.

* * * * *